(12) United States Patent
Huebler et al.

(10) Patent No.: US 7,938,007 B2
(45) Date of Patent: May 10, 2011

(54) METHOD FOR INSPECTING JOINED MATERIAL INTERFACES

(75) Inventors: James Emerson Huebler, Brookfield, IL (US); Maurice Givens, Chicago, IL (US)

(73) Assignee: Operations Technology Development, NFP, Des Plaines, IL (US)

( * ) Notice: Subject to any disclaimer, the term of this patent is extended or adjusted under 35 U.S.C. 154(b) by 514 days.

(21) Appl. No.: 12/117,143

(22) Filed: May 8, 2008

(65) Prior Publication Data

US 2009/0277270 A1     Nov. 12, 2009

(51) Int. Cl.
*G01N 29/04* (2006.01)
(52) U.S. Cl. .......................................... 73/622; 73/627
(58) Field of Classification Search .................. 73/588, 73/596–600, 602, 614–616, 622–629
See application file for complete search history.

(56) References Cited

U.S. PATENT DOCUMENTS

| | | | | |
|---|---|---|---|---|
| 3,895,685 A * | 7/1975 | Gillette et al. | ................. | 181/0.5 |
| 4,106,326 A * | 8/1978 | Lather et al. | .................. | 73/1.86 |
| 4,393,711 A * | 7/1983 | Lapides | ......................... | 73/592 |
| 4,480,475 A * | 11/1984 | Tsao et al. | ....................... | 73/610 |
| 4,588,873 A * | 5/1986 | Fenn et al. | .............. | 219/124.34 |
| 4,685,334 A * | 8/1987 | Latimer | ......................... | 73/599 |
| 6,332,361 B1 * | 12/2001 | Yamada et al. | ................. | 73/627 |
| 7,004,370 B2 * | 2/2006 | Arndt et al. | ....................... | 228/8 |
| 7,093,490 B2 * | 8/2006 | Kono et al. | ...................... | 73/602 |
| 7,188,526 B2 * | 3/2007 | Taylor et al. | .................... | 73/618 |
| 7,255,007 B2 * | 8/2007 | Messer et al. | .................. | 73/622 |
| 2007/0000328 A1 * | 1/2007 | Buttram | ......................... | 73/597 |
| 2009/0114021 A1 * | 5/2009 | den Boer | ........................ | 73/596 |

* cited by examiner

*Primary Examiner* — Helen C. Kwok
(74) *Attorney, Agent, or Firm* — Mark E. Fejer

(57) ABSTRACT

A method for inspecting joined material interfaces, such as butt fusion pipe joints of plastic pipes, using ultrasonic waveforms to discriminate between acceptable and unacceptable interfaces. The waveforms (amplitude vs time) having been transmitted to a material interface of interest are divided into a number of time zones and the amplitudes of the waveforms within the time zones compared against waveform amplitudes obtained from known acceptable joined material interfaces to determine the quality of the material interface of interest.

12 Claims, 5 Drawing Sheets

METHOD FOR INSPECTING JOINED MATERIAL INTERFACES

BACKGROUND OF THE INVENTION

1. Field of the Invention

In one aspect, this invention relates to the inspection of material interfaces for the purpose of assessing the quality of the interface. In one aspect of this invention, this invention relates to material interfaces which have been joined together, such as by bonding, heat fusion, electrofusion and the like. In a further aspect, this invention relates to joined interfaces between plastic pipe sections, joined interfaces between plastic pipes and plastic fittings connected with the plastic pipe, and a method for assessing the quality of the joined interfaces.

2. Description of Related Art

Plastic pipes have been in use for many years as a means for transporting underground utilities such as natural gas and water from place to place. The benefits of using plastic pipe include corrosion-resistance, ease of installation and relatively low costs compared with metal pipes. Plastic pipe sections are typically joined together using butt fusion joints, that is, joints arising from heating the plastic pipe ends and abutting the heated ends to fuse the pipe ends together, and using electrofusion couplings. Notwithstanding the many years during which plastic pipes have been employed, integrity of the butt fusion joints remains a significant concern among users.

Currently, butt fusion joints of plastic pipes are visually inspected and a joint is rejected if it is not the proper shape. Such visual inspection works in the majority of cases; however, there have been enough joint failures that the utilities want a better inspection method. Other than careful training in the production of butt fusion joints and visual inspection, there are no acceptable non-destructive inspection methods currently available. Non-destructive methods for assessing the quality of plastic pipe butt fusion joints in the past have tended to be expensive and complex to use, rendering them generally unacceptable. One ultrasonic method of testing butt fusion joints was developed by some natural gas utilities in the 1980's as a result of which a guideline standard (ASTM-F600-78) was issued for the manual ultrasonic inspection of butt fusion joints in polyethylene pipe. However, it was withdrawn in 1991 because the results were so heavily dependent upon the skill of the operator employing the method, rendering the results necessarily inconsistent and, thus, unreliable. The UltraMc® ultrasonic inspection tool, developed and marketed by McElroy Manufacturing, Inc. of Tulsa, Okla., was not a commercial success because it too required too much operator expertise. In addition, the UltraMc tool had difficulty detecting "cold joints". One solution that has been proposed for addressing this problem is removal of the butt fusion joint bead which is formed during the butt fusion process, polishing of the joint, and heating the joint area before applying the ultrasonic measurements. Although commercial ultrasonic equipment may be used by an expert operator to identify suspect butt fusion joints, the discrimination criteria vary significantly from operator to operator. In addition, such an approach is too expensive and, thus, rarely used.

SUMMARY OF THE INVENTION

Accordingly, it is one object of this invention to provide a non-destructive method for assessing the quality of butt fusion joints of plastic pipe which is easy to use and which requires substantially no input by the user.

It is another object of this invention to provide a method for assessing the quality of butt fusion joints of plastic pipe which does not require pretreatment or processing of the joints prior to use.

It is yet another object of this invention to provide a method for assessing the quality of electrofusion joints of plastic pipes.

These and other objects of this invention are addressed by a method for inspecting joined material interfaces comprising the steps of transmitting a plurality of acoustic waveforms onto a joined material interface at an angle greater than 0° and less than 90° with respect to an orientation or interface plane of the joined material interface; detecting a reflected waveform reflected from the joined material interface for each of the acoustic waveforms; dividing the acoustic waveforms into a plurality of time zones, with each time zone beginning at a time of detection of a corresponding reflected waveform and ending after a predetermined amount of time; determining a waveform amplitude for each acoustic waveform within each time zone; comparing the waveform amplitude against a predetermined waveform amplitude, which predetermined waveform amplitude represents a calibration amplitude for an acceptable joined material interface; and determining a quality of the joined material interface based upon the comparison of the waveform amplitude with the predetermined waveform amplitude.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

This invention involves the use of ultrasonic inspection as a means for discriminating between acceptable heat fusion joints and unacceptable, i.e. defective, heat fusion joints. To achieve the desired minimal expertise and training on the part of the operator, the method of this invention enables automatic analysis of waveforms and discrimination between acceptable and unacceptable fusion joints. Although the discussion of this invention is focused on butt fusion joints of plastic pipe, it is to be understood that the method of this invention may be employed in evaluating virtually any joint material interface, including applications involving the use of metal interfaces and interface bonding agents and other plastic pipe applications including electrofusion couplings, electrofusion saddle fittings, and heat fusion socket and saddle fittings, and such other joint material interfaces are deemed to be within the scope of this invention. For applications involving plastic pipe, the method of this invention is easily adaptable to different pipe diameters and different pipe materials.

Fusions between two pieces of plastic pipe may be inspected using acoustic waves. In accordance with preferred embodiments of this invention, such inspections are carried out using ultrasonic waveforms. The method of this invention utilizes waveforms reflected from the interface, referred to herein as pulse/echo, waveforms passing through the interface, referred to herein as pitch/catch, or both.

Figure 1:
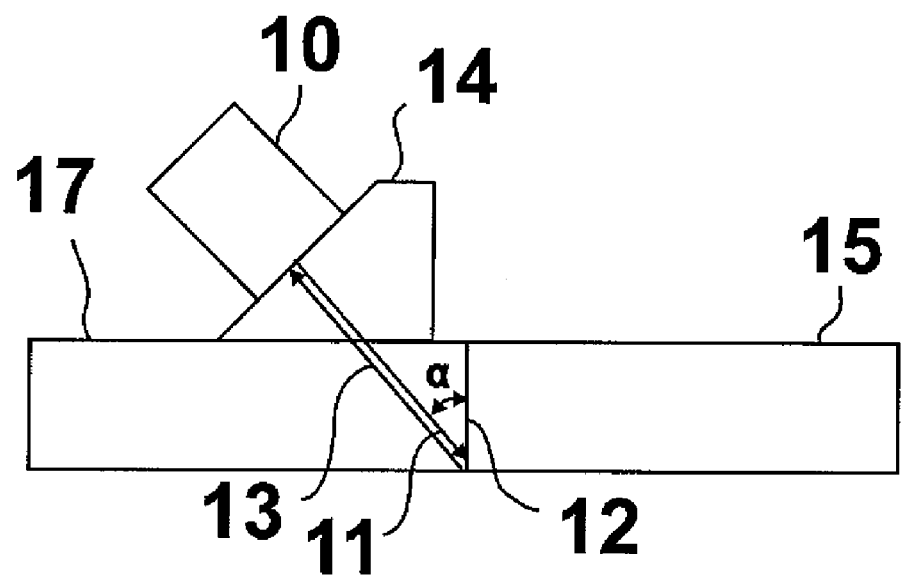
FIG. 1 is a diagram showing a pulse/echo acoustic transducer/receiver arrangement in accordance with one embodiment of this invention.

FIG. 1 shows a simplified diagram of one embodiment of the method of this invention for assessing butt fusion joints formed by the heat fusion of the ends of two pipe wall sections 15, 17 using a pulse/echo arrangement for transmission and detection of ultrasonic waveforms emitted by a transceiver 10. As shown therein, transceiver 10 emits one or more ultrasonic waveforms 11 which strike butt fusion joint 12, creating reflected waveforms 13 which are detected by transceiver 10. It will be appreciated that to ensure transmission of the ultrasonic waveform onto the butt fusion joint, ultrasonic waveform 11 is transmitted at an angle α greater than 0° and less than 90° relative to the orientation of butt fusion joint 12, which, depending upon the angle employed, may require more than two sensors. In accordance with one preferred embodiment, the angle of transmission of the ultrasonic waveform is in the range of about 40° to about 70°. In accordance with a particularly preferred embodiment, as shown in FIG. 1, the angle of transmission is about 45°. To provide the desired angle of incidence of the waveforms on the butt fusion joint 12, transmitter/receiver (i.e. transceiver) 10 is connected with a wedge shaped element 14 connected with pipe wall 15. One side of wedge shaped element 14 is disposed at an angle with respect to a horizontal of pipe wall 15 to which angled side transceiver 10 is connected. As well known in the art, the connection may be an ultrasonic couplant. The angled side of wedge shaped element 14 is oriented such that waveforms output from transceiver 10 are incident upon butt fusion joint 12. In accordance with one embodiment of this invention, wedge shaped element 14 is constructed of the same material as pipe wall 15.

Figure 2:
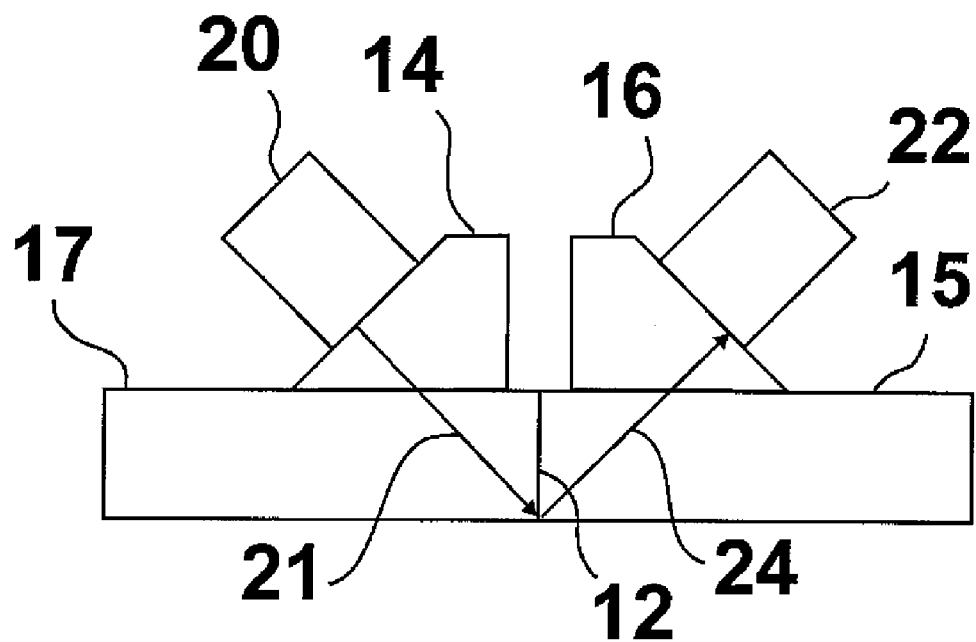
FIG. 2 is a diagram showing a pitch/catch acoustic transducer/receiver arrangement in accordance with one embodiment of this invention.

FIG. 2 shows a simplified diagram of one embodiment of the method of this invention for assessing butt fusion joints using a pitch/catch arrangement. As shown therein, transmitter 20, which is connected with the angled side of wedge shaped element 14, transmits (pitch) an ultrasonic waveform 21 which strikes and passes through butt fusion joint 12 providing a reflected waveform which is detected (catch) by a separate detector or receiver 22 connected with the angled side of a second wedge shaped element 16, also connected with pipe wall 15.

Although depicted as single waveforms in FIGS. 1 and 2, typically there are multiple paths for the waveforms with reflections from various parts of the joint. This results in complex waveforms that are difficult for an expert to completely interpret.

Figure 3:
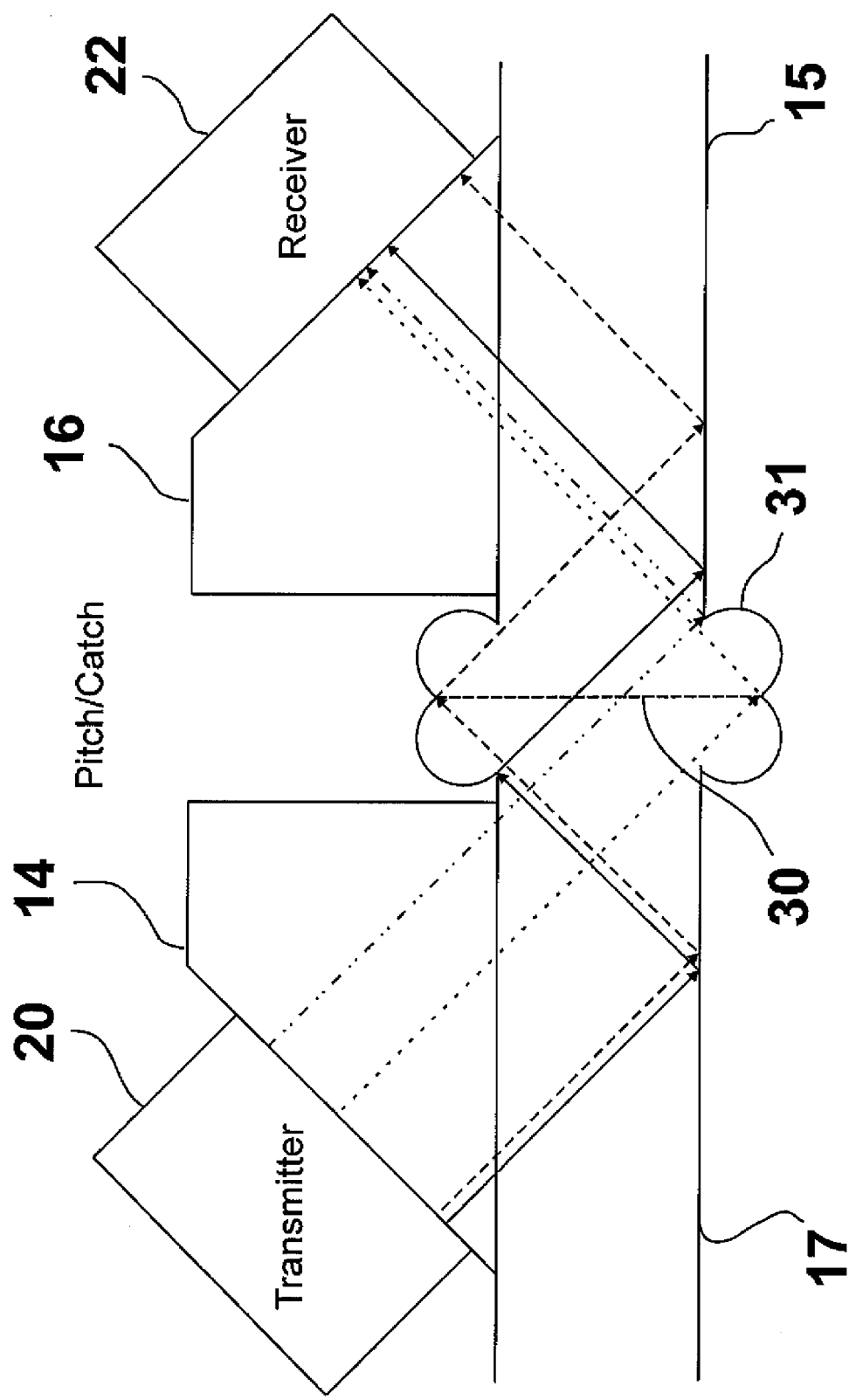
FIG. 3 is a cross-sectional view of a pipe wall and butt fusion joint showing the waveform paths occurring in a pitch/catch acoustic transmission and receiving arrangement.

FIG. 3 shows a cross-sectional view of a butt fusion joint 30 formed by two pipe wall segments 15, 17. In a properly formed butt fusion joint, the heated ends of the pipe segments to be joined are pushed together with adequate force such that a portion of the heated ends is expelled from between the heated ends resulting in the formation of a fusion bead 31. A properly formed heat fusion joint will have a fusion bead uniform in size and shape evenly distributed around the joined pipe segments. FIG. 3 also shows the waveform paths occurring in a pitch/catch system for properly formed butt fusion joint.

Figure 4:
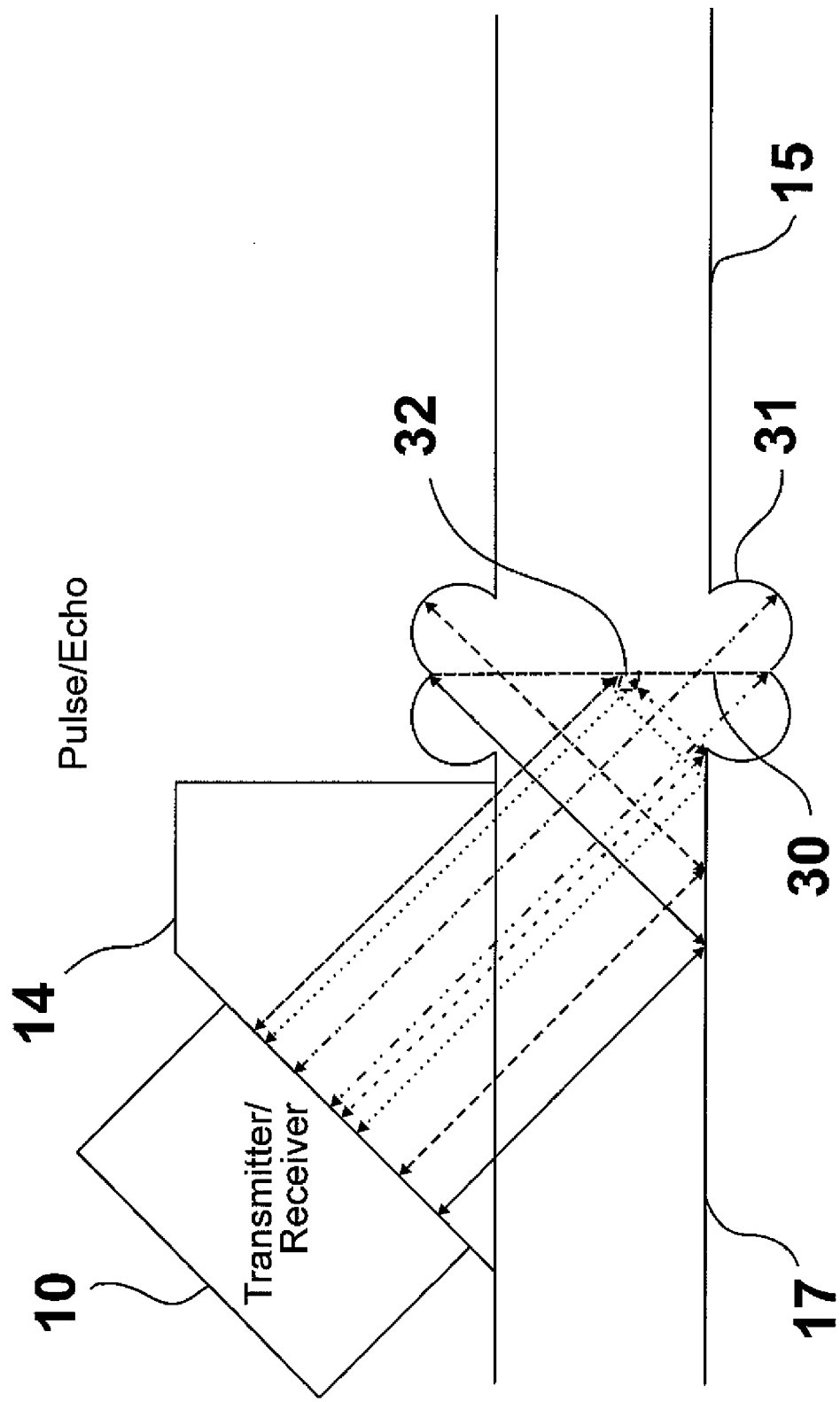
FIG. 4 is a cross-sectional view of a pipe wall and butt fusion joint showing the waveform paths occurring in a pulse/echo acoustic transmission and receiving arrangement.
Figure 5:
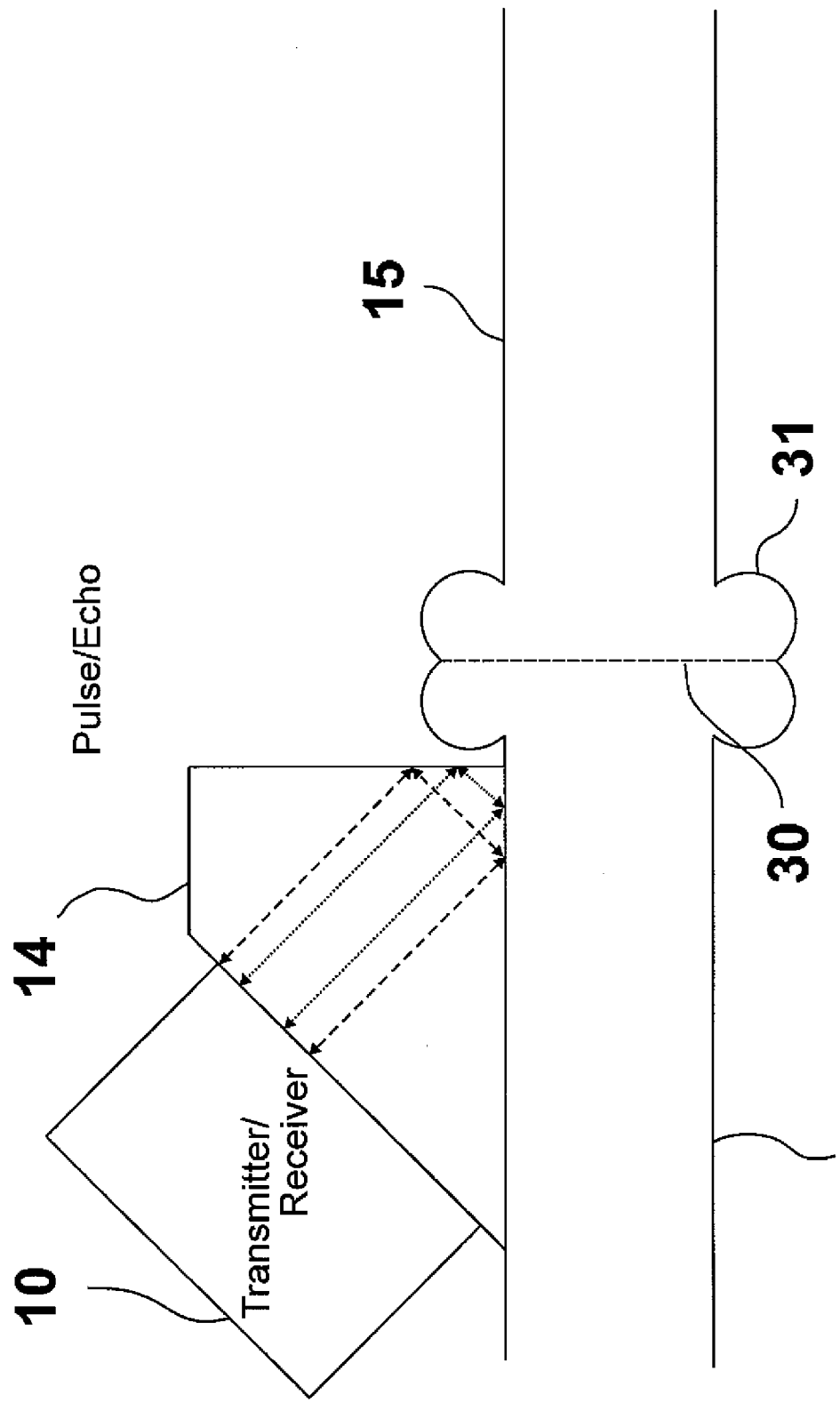
FIG. 5 is a cross-sectional view of a pipe wall and butt fusion joint showing additional possible waveform paths for a pulse/echo transmission and receiving arrangement.

FIG. 4 shows a cross-sectional view of a butt fusion joint 30 formed by two pipe wall segments 15, 17. In the embodiment of the invention shown in FIG. 4, a pulse/echo arrangement of the acoustic transmitter and receiver is employed for generation of the waveform paths. Also shown in FIG. 4 is a defect 32 and the impact of the defect on the waveform paths. FIG. 5 shows the waveform paths occurring within wedge shaped element 14 under conditions where the interface between the wedge shaped element and the pipe wall is less than acceptable.

Figure 6:
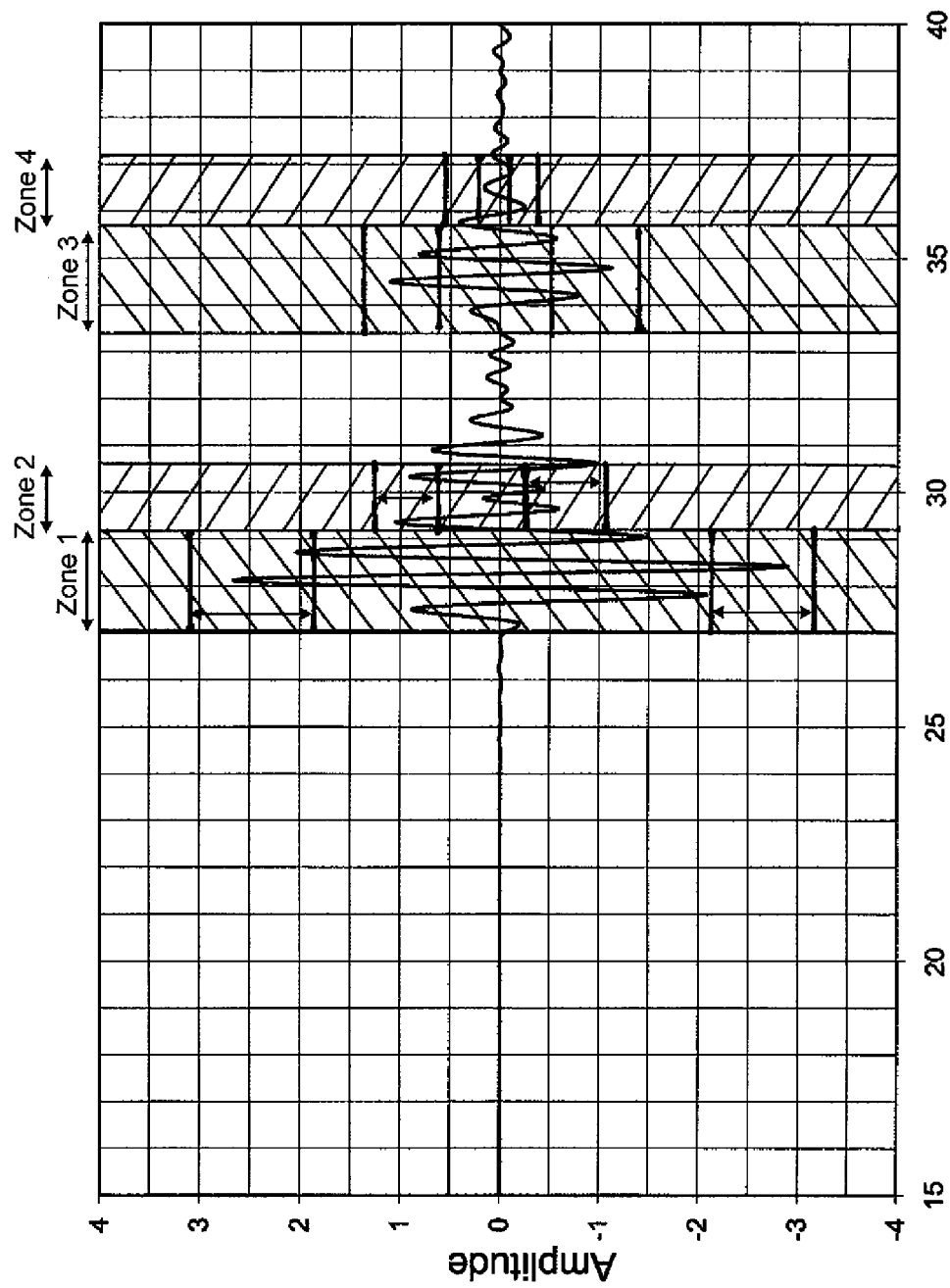
FIG. 6 is a diagram illustrating the zones and zone levels for a pitch/catch waveform.

The method of this invention divides the waveforms (amplitude vs time) produced by the ultrasonic equipment into a plurality of time zones. FIG. 6 shows one example of the time zones as discussed in more detail herein below for an ultrasonic waveform in accordance with one embodiment of this invention. As shown therein, the time zones do not have to cover all of the waveform. Waveforms from acceptable butt fusion joints will have a limited range of amplitude values in each time zone. Waveforms from unacceptable butt fusion joints will have amplitude values outside the acceptable limits within some of the time zones. Combining the results from all of the time zones permits discrimination between the acceptable and unacceptable butt fusion joints. In some cases, the method of this invention may even be used to identify the specific flaw or flaws in the joint. It will be appreciated that the method of this invention may be used with acoustic waveforms other than ultrasonic waveforms and may be used in other applications.

FIG. 6 shows exemplary zones and zone levels for a pitch/catch waveform. The shaded areas represent the zones and pairs of bars across each zone represent the amplitude ranges for an acceptable butt fusion joint. In this example, each zone has two pairs of bars, one for the positive portion of the waveform and the other for the negative portion of the waveform. The zones are derived based upon an assumption that ultrasonic waves propagate as rays. A ray diagram of the waveform paths in the polyethylene wedge shaped element 14 and the pipe wall 15 is shown in FIG. 3. Measurements of the velocity of sound were used to predict the time of arrival for each waveform path. The time of arrival represents the start of the time zone. The initial wave propagating into the material is not a delta function, but rather is composed of multiple cycles. In this example, the initial waveform was 5 cycles of a 2.25 MHz resonant frequency of the sensor. The length of the zones was selected to be 2.2 microseconds long (corresponding to 5 periods of a 2.25 MHz sine wave). When zones overlap as shown in FIG. 6, some of the zones are shortened. Typically, the criteria for selecting which zone to shorten can be based on the most physically meaningful wave path. However, it may also be selected by processing the waveforms to determine which gives the best results.

In this example, following selection of the time zones, the next step was to produce butt fusion joints of the appropriate quality and collect, i.e. detect, the waveforms derived from application of the ultrasonic waveforms to the butt fusion joints. Nine joints were produced including joints of acceptable quality as determined by visual inspection and joints having intentionally introduced flaws. The purpose of this step was to establish the criteria against which measurements made on subsequent butt fusion joints for a given material and material thickness could be compared. In practice, such criteria will already have been entered into the system employed for assessing the quality of the butt fusion joints.

In the case of butt fusion joints, we have identified thirteen possible waveform paths as shown in FIGS. 3, 4 and 5—seven paths in the pulse/echo wave, four in the pitch/catch wave, and two in the wedge itself if the coupling of waves from the wedge into the pipe is bad. From the nine joints, we collected 53 waveforms, thirteen of which were considered to be from acceptable fusion joints. The waveforms were then processed by a program to determine the range of amplitudes in each time zone. The amplitudes fell within two ranges for each of the thirteen time zones—one range for positive excursions of the wave, represented by the pair of bars in the positive amplitude range as shown in FIG. 6, and one range for negative excursions of the wave, represented by the pair of bars in the negative amplitude range also shown in FIG. 6. The result was twenty-six amplitude ranges for use in comparing the results obtained from other butt fusion joints. The waveforms are not symmetric, thus the values of positive and negative excursions are not necessarily the same.

Following identification of the twenty-six amplitude ranges, a twenty-six element vector was formed using both ranges in each time zone, assigning a value of +1 if the wave amplitude exceeds the range, 0 if the wave amplitude is within the range, and −1 if the wave amplitude is below the range. A computer program was used to automatically determine which value (+1, 0, −1) applied for each of the twenty-six ranges. An acceptable joint should be 0 for all twenty-six vector elements. We then ran the 53 waveforms that we had previously collected through the computer program and compared the results against visual inspection and known introduced flaws. The vector predictions accurately identified 48 of the 53 waveforms. In those cases in which the prediction of joint quality differed from that predicted by the 26 element vector, we believe that some of the waveforms visually classified as acceptable are, in fact, unacceptable. Thus, the method of this invention enables the use of simple +1, 0, −1 criteria for the amplitude values. It is, however, possible to make use of the amount the amplitude falls outside of the range and/or to weight the values of the vector elements.

We have applied the method of this invention to different polyethylene materials with different pipe wall thicknesses and, after adjusting the time zones and ranges (high density polyethylene has different velocity of sound and attenuation than medium density polyethylene), we found that the method worked equally well in both cases.

It will be appreciated that amplitudes of various portions of the waveforms are affected by transmission/reflection properties of the fusion plane and by the shape of the inner and outer beads formed by the fusion process. It is possible in some cases to look at the type and location of a flaw and estimate whether the amplitude in some zones should be greater or smaller than for an acceptable joint. In other cases, the shape of the beads and the transmissive properties of the fusion plane are too complex to make a prediction. As an initial test of typing capability, we used the method of this invention to type flaws in the butt fusion joints and we found that the method could be successfully used for several types of flaws. Tables 1, 2 and 3 show the effectiveness of this method and provide the results of a few of the classifications. For most flaws, several values of the vector are not 0; that is, the rejection results are robust. The first set of letters A through G corresponds to pulse/echo paths where the amplitudes are positive. The second set corresponds to pulse/echo paths where the amplitudes are negative. H and I refer to ultrasonic paths entirely in the wedge. The first set of numbers 5, 8, 11, and 12 corresponds to pitch/catch paths where the amplitudes are positive. The second set corresponds to pitch/catch paths where the amplitudes are negative. Each row vector corresponds to a pipe section where the waveform was measured.

Readings are collected at several positions around the circumference of a butt fusion joint. Each vector represents the results at one position. As previously indicated, fifty-three vectors were generated from nine butt fusion joints. Table 1 shows the results obtained from ten positions around a butt fusion joint which was determined by visual inspection to be acceptable. Because the measurements at each of the ten positions represent a good butt fusion joint, all of the values in each vector are zero.

Table 2 shows the results obtained from five positions around a butt fusion joint at which positions one or more objects are discontinuities in the fusion plane were present. These flaws in the fusion plane ranged from a single blade of grass to a thin sheet of plastic having properties dissimilar to the properties of the polyethylene pipe being fused. Discontinuities in the fusion plane cause an increased reflection in the pulse/echo waveform for positive values of vector D and a corresponding decrease in transmission through the fusion plane at both positive and negative values of vector 5. Depending on the causes of the discontinuities, there are increases in amplitude at vector values for E and decreases in amplitude at vector values for 8.

Table 3 shows the vectors collected at six positions around the same butt fusion joint. This joint was made by properly preparing and heating the pipe ends; however, the two pipes were misaligned upon being fused together. This misalignment resulted in variations in joint quality around the joint circumference. Each vector has non-zero values, which indicates that the fusion was bad at all positions. The non-zero values are at different elements of the vector because the offset affects the bead shape differently at different positions. Thus, there is no obvious pattern in the vectors around the circumference of the fusion joint.

TABLE 1

Vectors for Good Butt Fusion Joints

| A | B | C | D | E | F | G | H | I | 5 | 8 | 11 | 12 | A | B | C | D | E | F | G | H | I | 5 | 8 | 11 | 12 |
|---|---|---|---|---|---|---|---|---|---|---|---|---|---|---|---|---|---|---|---|---|---|---|---|---|---|
| [0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0] |
| [0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0] |
| [0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0] |
| [0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0] |
| [0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0] |
| [0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0] |
| [0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0] |
| [0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0] |
| [0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0] |
| [0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0] |

TABLE 2

Vectors for Joints with One or More Foreign Objects in the Fusion Plane

| A | B | C | D | E | F | G | H | I | 5 | 8 | 11 | 12 | A | B | C | D | E | F | G | H | I | 5 | 8 | 11 | 12 |
|---|---|---|---|---|---|---|---|---|---|---|----|----|---|---|---|---|---|---|---|---|---|---|---|----|----|
| [0 | -1 | 0 | 1 | 1 | 0 | 0 | 0 | 1 | -1 | -1 | 0 | -1 | 0 | 0 | 0 | 1 | 1 | -1 | 0 | 0 | 0 | -1 | -1 | 0 | 0] |
| [0 | -1 | 0 | 1 | 1 | 0 | 0 | 0 | 0 | -1 | -1 | 0 | 0 | 0 | 0 | 0 | 1 | 1 | 0 | 0 | 0 | 0 | -1 | -1 | 0 | 0] |
| [0 | 0 | 0 | 1 | 0 | 0 | 0 | 0 | 1 | -1 | 0 | 1 | 1 | 0 | 0 | 0 | 0 | 0 | 0 | 0 | 0 | 0 | -1 | 0 | 1 | 1] |
| [0 | 0 | -1 | 1 | 0 | 0 | 0 | 0 | 1 | -1 | -1 | 0 | 0 | 0 | 0 | 0 | 0 | 1 | 0 | 0 | 0 | 0 | -1 | -1 | 0 | 0] |
| [0 | 0 | 0 | 1 | 0 | 0 | 0 | 0 | 0 | -1 | -1 | 0 | 0 | 0 | 0 | 0 | 0 | 1 | 0 | 0 | 0 | 0 | -1 | -1 | 0 | 0] |

TABLE 3

Vectors for Misalignment of Pipe Ends

| A | B | C | D | E | F | G | H | I | 5 | 8 | 11 | 12 | A | B | C | D | E | F | G | H | I | 5 | 8 | 11 | 12 |
|---|---|---|---|---|---|---|---|---|---|---|----|----|---|---|---|---|---|---|---|---|---|---|---|----|----|
| [0 | 0 | -1 | 0 | 0 | 0 | -1 | 0 | 0 | -1 | 0 | 0 | -1 | 0 | 0 | -1 | 0 | 1 | 0 | 1 | 0 | 0 | -1 | 1 | 0 | 0] |
| [0 | -1 | 0 | 0 | 0 | 0 | -1 | 0 | 1 | 0 | 0 | 0 | 0 | 0 | 0 | 0 | 0 | 1 | 0 | 0 | 0 | 0 | 0 | 0 | 0 | 0] |
| [0 | 0 | -1 | 0 | 0 | 0 | 0 | 0 | 1 | 0 | 0 | 0 | 0 | 0 | 0 | 1 | 0 | 1 | 0 | 0 | 0 | 0 | 0 | 0 | 0 | 0] |
| [0 | 0 | 0 | 0 | 0 | 0 | 0 | 0 | 0 | 1 | -1 | 0 | 0 | 0 | 0 | 0 | 0 | 0 | 0 | 0 | 0 | 0 | 0 | 1 | -1 | -1] |
| [0 | -1 | 0 | 0 | 0 | 0 | 0 | 0 | 1 | -1 | 0 | 0 | 0 | 1 | 0 | 0 | 1 | 0 | 0 | 0 | 0 | -1 | 0 | 0 | 0 | 0] |
| [0 | -1 | -1 | 0 | 0 | 0 | -1 | 0 | 1 | 0 | 1 | 0 | 0 | 0 | 0 | 0 | 1 | 0 | 0 | 0 | 0 | 0 | 0 | 0 | 0 | 0] |

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A method for inspecting joined material interfaces comprising the steps of:
    transmitting a plurality of acoustic waveforms onto a joined material interface at an angle greater than 0° and less than 90° with respect to an orientation of said joined material interface;
    detecting a reflected waveform reflected from said joined material interface for each of said acoustic waveforms;
    dividing said acoustic waveforms into a plurality of time zones, each said time zone beginning at a time of detection of a corresponding said reflected waveform and ending after a predetermined amount of time;
    determining a waveform amplitude for each said acoustic waveform within each said time zone;
    comparing said waveform amplitude against a predetermined waveform amplitude, said predetermined waveform amplitude representing a calibration amplitude for an acceptable said joined material interface; and
    determining a quality of said joined material interface based upon said comparison of said waveform amplitude with said predetermined waveform amplitude.

2. The method of claim 1, wherein said acoustic waveform is an ultrasonic waveform.

3. The method of claim 1, wherein said joined material interface comprises a plastic material.

4. The method of claim 1, wherein said joined material interface is a fusion joint.

5. The method of claim 1, wherein said joined material interface is a fusion joint selected from the group consisting of heat fusion joints, electrofusion joints, and combinations thereof.

6. The method of claim 1, wherein said joined material interface is a butt fusion joint.

7. The method of claim 6, wherein said joined material interface comprises two sections of plastic pipe.

8. The method of claim 7, wherein said plastic pipe is a polyethylene pipe.

9. The method of claim 1, wherein a transmitter of said acoustic waveform and a detector of said reflected waveform are disposed in a pulse/echo arrangement.

10. The method of claim 1, wherein a transmitter of said acoustic waveform and a detector of said reflected waveform are disposed in a pitch/catch arrangement.

11. The method of claim 1, wherein said angle is in a range of about 40° to about 70°.

12. The method of claim 1, wherein said angle is about 45°.

* * * * *